United States Patent
Fassi et al.

(12) 
(10) Patent No.: US 6,255,346 B1
(45) Date of Patent: Jul. 3, 2001

(54) COMPOSITION FOR SUPPRESSING WITHDRAWAL SYMPTOMS AND CRAVING FOR ALCOHOL IN ALCOHOLICS AND PREVENTING THE ABUSE OF ALCOHOL IN HEALTHY SUBJECTS

(75) Inventors: Aldo Fassi, Pomezia; Claudio Cavazza, Rome, both of (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/509,652

(22) PCT Filed: Sep. 18, 1998

(86) PCT No.: PCT/IT98/00249

§ 371 Date: Jun. 6, 2000

§ 102(e) Date: Jun. 6, 2000

(87) PCT Pub. No.: WO99/17623

PCT Pub. Date: Apr. 15, 1999

(30) Foreign Application Priority Data

Oct. 3, 1997 (IT) .............................................. RM97A0594

(51) Int. Cl.[7] .................................................... A01N 37/12
(52) U.S. Cl. ............................................................ 514/561
(58) Field of Search ............................................. 514/561

(56) References Cited

FOREIGN PATENT DOCUMENTS 195 27 281   1/1997  (DE) .
0 517 125   12/1992  (EP) .
0 793 962    9/1997  (EP) .

OTHER PUBLICATIONS

Tempesta et al, (II) Int. J. Clin. Pharmacol Res., vol. 10, pp 1–2 (abstract), 1990.*
Conte et al, Int. J. Tissue React., vol. 17, pp. 21–31 (abstract), 1995.*
Tempesta E., et al, "Role of acetyl–L–carnitine in the treatment of cognitive deficit in chronic alcoholism" *International Journal of Clinical Pharmacology Research*, vol. 10, No. 1/2, 1990, pp. 101–107.
Abu Murad C., et al, "Hepatic trigylceride accumulation and the ethanol physical withdrawal syndrome in mice", *British Journal of Experimental Pethology*, vol. 58, No. 6, 1977, p. 606–615.
Corbett R. and Leonard B.E., "Effects of carnitine on changes caused by chronic administration of alcohol", *Neuropharmacology*, vol. 23, No. 2B, 1984, p. 269–271.
Schmidl M K et al, "Medical Foods", *Food Technology*, vol. 46, No. 4, Apr. 1992, pp. 87–96.
Leibovitz B et al, "Carnitine" *Journal of Optimal Nutrition*, vol. 2, No. 2, 1993, pp. 90–109.

* cited by examiner

*Primary Examiner*—James H. Reamer
(74) *Attorney, Agent, or Firm*—Nixon & Vanderhye P.C.

(57) ABSTRACT

A combination composition comprising L-carnitine, acetyl L-carnitine and propionyl L-carnitine or the pharmacologically acceptable salts thereof is disclosed which can be used as a pharmaceutical composition for suppressing withdrawal symptoms and craving for alcohol in alcoholics, and as a dietary supplement, health food, medical food or nutraceutical for preventing the abuse of alcohol in substantially healthy subjects, particularly in young individuals.

13 Claims, No Drawings

COMPOSITION FOR SUPPRESSING WITHDRAWAL SYMPTOMS AND CRAVING FOR ALCOHOL IN ALCOHOLICS AND PREVENTING THE ABUSE OF ALCOHOL IN HEALTHY SUBJECTS

This application is a 35 U.S.C. § 371 of PCT/IT98/00249, filed Sep. 18, 1998.

The present invention relates to a combination composition of L-carnitine and lower alkanoyl L-carnitines or the pharmacologically acceptable salts thereof for the treatment of alcoholism. The use of the combination composition suppresses withdrawal symptoms (such as tremors, perspiration, hyperreflexia, nausea, anxiety and convulsions) and the craving for alcohol.

All the drugs used to date for the treatment of alcoholism present substantial drawbacks.

A number of the drugs commonly used in the treatment of alcohol withdrawal syndrome are similar to this with regard to their pharmacological effects. In fact, the most useful of those currently used are those with which alcohol develops a cross-tolerance. All patients treated for withdrawal syndromes are potential candidates for SNC depressants though not all of them need them.

Paraldehyde, which was once extensively used in therapy, was completely abandoned on account of its disagreeable odour and a series of sudden, inexplicable deaths following its use.

Rarely used today is the fast-acting barbiturate (pentobarbital and secobarbital).

The drugs of choice are benzodiazepines such as chlorodiazepoxide and diazepam. One serious drawback they present, however, is the fact that alcoholics taking chlordiazepoxide or diazepam may become intoxicated and even develop physical addiction and withdrawal syndrome.

The phenothiazines are not recommended since they do not control severe delirium tremens and also lower the threshold for attacks of epilepsy.

Lastly, a matter of some controversy is the therapeutic use of disulfiram which interferes with the metabolism of acetaldehyde (an intermediate product of the oxidation of alcohol) and produces an accumulation of it, thus causing toxic symptoms and severe discomfort. Drinking alcohol within 12 hours of taking disulfiram produces facial flushing within 5–15 minutes, followed by intense vasodilatation of the face and neck with clouding of the conjunctiva, throbbing headache, tachycardia, hyperpnoea and perspiration. Within 30–60 minutes nausea and vomiting appear and can be so intense as to lead to hypertension, dizziness and sometimes fainting or collapse. The reaction lasts from one to three hours. The sense of malaise is so intense that few patients will risk drinking alcohol while taking disulfiram. Occasionally, this drug has also caused convulsions, cardiac arrhythmias and myocardial infarction.

The efficacy of carnitine in decreasing the withdrawal symptoms in test animals has been reported.
Abu Murad et al. (Brit. J. Pathol. vol. 58. n. 6, Dec. 1977) discloses that in mice "the addition of DL-carnitine to diet during the administration of ethanol . . . significantly reduced the intensity of the ethanol withdrawal syndrome". Corbett et al. (Neuropharmacology, vol. 23, n. 2B, pp. 269–271, 1984) postulate that carnitine administration can counteract "at least some of the effects of prolonged administration and withdrawal of ethanol . . . by preventing the alcohol-induced change in the activity of (calcium/magnesium) ATPase".

As regards acetyl L-carnitine, Tempesta et al. (Int. J. Clin. Pharm. Res. X (1/2) 101–107, 1990) report preliminary data from a multicentred double-blind placebo-controlled study which suggest a possible efficacy of acetyl L-carnitine in decreasing some cognitive deficits in at least one month-abstinent chronic alcoholics.

The efficacy of other alkanoyl L-carnitines, particularly propionyl L-carnitine, in the treatment of alcoholics, has never been postulated nor tested.

It has now been found that a combination composition comprising L-carnitine, acetyl L-carnitine, propionyl L-carnitine or the pharmacologically acceptable salts thereof not only suppresses the withdrawal symptoms (such as tremors, perspiration, hyperreflexia, nausea, anxiety and convulsions) and the craving for alcohol in alcoholics, but can also be used effectively as a preventive or prophylactic means in substantially healthy subjects who, however, overindulge in an excessive, although occasional and discontinuous, intake of alcoholic drinks.

It is worth noticing that the users of the compositions of the present invention may also be substantially healthy individuals, particularly young subjects, who, although they cannot be clinically regarded as alcohol-addicted, occasionally indulge in an excessive intake of strongly alcoholic drinks under circumstances which take place more frequently than in the past, as a consequence of the profound changes in lifestyle which have occurred, particularly with regard to young individuals, over a relatively short space of time. This phenomenon can affect important aspects of family life as well as social and personal relations, with worrying consequences even of a socio-economic nature.

The combination compositions of the present invention can, therefore, occur not only as pharmaceutical compositions but also as dietary supplements, health foods, medical foods or nutraceuticals or as components of the aforesaid products. Then, the compositions may also comprise, in admixture with L-carnitine and the aforesaid alkanoyl L-carnitines, further active ingredients, such as dietary supplements, vitamins, co-enzymes, minerals and the like.

The molar ratio L-carnitine/acetyl L-carnitine/propionyl L-carnitine or the pharmacologically acceptable salts thereof ranges from 6:4:1 to 3:2:1. Preferable, this ratio is 5:4:1.

In unit dosage forms, the compositions comprise 0.44 to 0.66 g of L-carnitine inner salt; 0.44 to 0.66 g of acetyl L-carnitine inner salt; and 0.12 to 0.18 g of propionyl L-carnitine inner salt or equimolar amounts of their pharmacologically acceptable salts.

What is meant by pharmacologically acceptable salt of L-carnitine, acetyl L-carnitine and propionyl L-carnitine is any salt of these active ingredients with an acid that does not give rise to unwanted toxic or side effects. These acids are well known to pharmacy experts.

Non-limiting examples of suitable salts are the following: chloride; bromide; iodide; aspartate, particularly acid aspartate; citrate, particularly acid citrate; tartrate; phosphate, particularly acid phosphate; fumarate, particularly acid fumarate; glycerophosphate; glucose phosphate; lactate; maleate, particularly acid maleate; orotate; oxalate, particularly acid oxalate; sulphate, particularly acid sulphate; trichloroacetate; trifluoroacetate and methanesulphonate.

A list of FDA-approved pharmacologically acceptable salts is given in Int. J. of Pharm. 33, (1986), 201–217; this latter publication is incorporated herein by reference.

Since L-carnitine and the aforesaid alkanoyl L-carnitine are practically atoxic, the combination composition of the present invention does not bring about any of the previously mentioned unwanted toxic or side effects.

Reported here below are details of a number in-vivo pharmacological studies which demonstrate the activity of the combination composition of the present invention, vis-a-vis L-carnitine and acetyl L-carnitine taken singularly.

In the following description "COMP" stands for the combination composition, "LC" for L-carnitine, "ALC" for acetyl L-carnitine and "PLC" for propionyl L-carnitine.
Sedative Action COMP in Alcohol-Dependent Rats as Measured According to the Vogel Test.

Wistar male rats (housed in groups of 5 per cage) were used, kept in conditions of constant light-dark alteration at 21° C. and fed with standard laboratory feed. The animals were chronically administered 10% ethanol ad lib. for 6 months.

To assess the activity, if any, of COMP on the anxiety component involved in the compulsive act of searching for alcohol, a modified version of the Vogel test was used as described by Keppler D. et al. in Exp. Mol. Path. 9, 279 (1968).

Prior to the start of the experiment the animals were deprived of water for 48 hours. At the time of ethanol treatment suspension, the animals were divided into 4 groups who were given the following intraperitoneal administrations: the first group (A) received saline solution (15 ml/kg), the second group (B) COMP (20 mg LC+20 mg ALC+4 mg PLC/kg), the third group (C) LC (20 mg/kg) and the fourth group (D) ALC (20 mg/kg).

On the day of the test, the animals were provided with two drinking vessels, one containing water and the other a mixture of water and ethanol (90:10 v/v) in bottles, the metal spouts of which were connected up to a source of electricity: after every 5 licks at the drinking vessel, and electric shock (1 mA) was delivered for 10 min. which obliged the animal to withdraw, overcoming its desire to drink the water-alcohol solution. Refusal of the animal to drink the water-alcohol solution, confining their attention only to the vessel containing water alone, was taken as an indication of efficacy. In evaluating the results, the numbers of licks were compared for treated animals versus controls over the 10 min. exposure period. The results are given here below in Table 1.

TABLE 1

Number of licks of treated animals over 10 min. exposure period

| Animal group | Number of licks |
| --- | --- |
| A (saline) | 39.8 ± 7.5 |
| B (COMP) | 4.9 ± 1.14* |
| C (LC) | 10 ± 6.4* |
| D (ALC) | 32.2 ± 6.4 |

*P < 0.01 vs A
P < 0.05 vs B

Effects of COMP on Withdrawal Syndrome in Rats as Measured by the Hunt-Majchrowicz Method.

The experiment was performed in Wistar male rats housed in groups of 5 per cage under conditions of constant light-dark alternation at 21° C. and fed with standard laboratory feed. The animals were chronically administered 10% ethanol ad lib. for 6 months.

Eight hours after suspension of ethanol administration, the animals were divided into 4 groups of 5 rats each.

The first group (A) was administered saline solution intraperitoneally (15 ml/kg), the second group (B) was given COMP. (20 mg LC+20 mg ALC+4 mg PLC/kg), again intraperitoneally, the third group (C) received LC (20 mg/kg), while he fourth group (D) was given ALC (20 mg/kg). For the purposes of assessing the effects induced by the above-mentioned treatments on occurrence of alcohol withdrawal syndrome, tremors were measured in the rat, where, as in man, they are the most characteristic sign of withdrawal syndrome. Evaluation of the number of tremors was done using the method described by Hunt and Majchrowicz [see Hunt W. A. and Majchrowicz E., Journal of Pharmacology and Experimental Therapeutics, 213, 9–12 (1980)]. The results are given here below in Table 2.

TABLE 2

| Animal group | 30 min. | 60 min. | 90 min. | 120 min. |
| --- | --- | --- | --- | --- |
| A (saline) | 6 ± 1.5 | 9 ± 2.5 | 8 ± 2.5 | 9 ± 1.5 |
| B (COMP) | 0 ± 0.25 | 0 ± 0 | 0 ± 0.65 | 0 ± 0.25 |
| C (LC) | 2 ± 0.5 | 1 ± 0.5 | 2 ± 1 | 3 ± 1 |
| D (ALC) | 4 ± 2 | 5 ± 2 | 5 ± 1.5 | 6 ± 2 |

Effects of COMP on withdrawal syndrome as assessed by observing behaviour of rats chronically treated with alcohol when subjected to sound stimulation.

The experiment was performed in Wistar male rats housed in groups of 5 per cage under constant light-dark alternation at 21° C. and fed with standard laboratory feed. The animals were chronically administered 10% ethanol ad lib. for 6 months.

Eight hours after suspension of ethanol administration the animals were divided into 4 groups of 10 rats each.

The first group (A) were administered saline solution (15 ml/kg) intraperitoneally, the second group (B) COMP (20 mg LC+20 mg ALC+4 mg PCL/kg) again intraperitoneally, the third group (C) LC (20 mg/kg) and the last group (D) ALC (20 mg/kg). For the purposes of evaluating the effects of the treatment on occurrence of alcohol withdrawal syndrome, the rats' susceptibility to onset of behavioural reactions (convulsions) due to emission of sound for 1 min. by an electric bell (100 dB) was observed. The experiment was performed in all groups of rats one hour after treatment, and the results are given here below in Table 3.

TABLE 3

| Animal group | Animals with convulsions/ animals treated |
| --- | --- |
| A (saline) | 8/10 |
| B (COMP) | 1/10 |
| C (LC) | 5/10 |
| D (ALC) | 6/10 |

Effects of COMP on lipoperoxidation in the CNS of rats receiving chronic ethanol treatment.

This study was conducted in order to assess what variations in malonaldehyde (MDA) occur following COMP administration, MDA being a reliable and quantifiable index of the vulnerability of the central nervous system to damage due to free radicals as a result of the detrimental effect of ethanol.

The experiment was conducted in Wistar male rats housed in group of 5 per cage under constant light-dark alternation at 21° C. and fed with standard laboratory feed. Two groups of rats, each comprising 5 animals, were administered 10% ethanol in water throughout the treatment period. A third group of animals was kept on a standard laboratory diet without receiving any treatment. After two months of ethanol treatment, the animals in the first group were administered COMP (20 mg LC+20 mg ALC+4 mg PLC/kg) in a single intraperitoneal dose. A few hours after treatment, the animals were sacrificed and the brains promptly removed. MDA was measured using a modified micromethod described by Slater and Sawyer (Slater T. F. and Sawyer B.

C., 1971, J. Biochem. Tokyo 8: 2180). The tissue was held for 10 min. at 0° C. in Tris-HCl 0.05 M buffer at pH 7.4 and then homogenized. An aliquot (0.05 ml) of cerebral homogenate was extracted with 20% trichloroacetic acid (w/v). After centrifuging, 0.9 ml of supernatant were added to 1 ml of 0.67% thiobarbituric acid in Tris-HCl 0.026 M buffer at pH 7.0. The samples were placed in boiling water for 10 minutes and after cooling absorbance was determined at 532 nm using a spectrophotometer. MDA was expressed in nmol/mg protein. Proteins were measured by the Smith method (Smith at al., 1985, Analyt. Biochem. 27: 502), using bicinchoninic acid as reagent. Table 4 here below shows the amount of MDA in control animals, in animals after administration of ethanol and in animals after administration of ethanol+COMP.

TABLE 4

| Animal group | MDA nmol/mg protein |
| --- | --- |
| Control | 0.543 ± 0.19 |
| Ethanol | 1.12 ± 0.13 |
| Ethanol + COMP. | 0.385 ± 0.15 |

The composition of the present invention can be administered orally or parenterally, in any of the usual pharmaceutical forms which are prepared by conventional procedures well-known to the experts in these techniques. These forms comprise oral unit dosage forms, both liquid and solid, such as tablets, capsules, solutions, syrups and the like, and injectable forms such as, for example, sterile solutions for vials and ampoules.

For these pharmaceutical forms the usual solvents, diluents and excipients are used. Optionally, preservative, sweetening and flavouring agents can be added. Non-limiting examples of such substances are sodium carboxymethyl cellulose, polysorbate, sorbitol, starch avicel, talc and others which are evident to experts in pharmaceutical technology.

What is claimed is:

1. An orally or parenterally administrable composition comprising in admixture L-carnitine, acetyl L-carnitine and propionyl L-carnitine or the pharmacologically acceptable salt thereof.

2. The composition of claim 1 as a dietary supplement, health food, medical food, nutraceutical or component thereof for preventing the abuse of alcohol in substantially healthy subjects.

3. The composition of claim 1, wherein the molar ratio L-carnitine:acetyl L-carnitine:propionyl L-carnitine or the pharmacologically acceptable salts thereof ranges from 6:4:1 to 3:2:1.

4. The composition of claim 3 wherein said ratio is 5:4:1.

5. The composition of claim 3 in unit dosage form comprising from 0.44 to 0.66 g L-carnitine inner salt; 0.44 to 0.66 g of acetyl L-carnitine inner salt; and from 0.12 to 0.18 g of propionyl L-carnitine inner salt or equimolar amounts of the pharmacologically acceptable salts thereof.

6. The composition of claim 1 wherein the pharmacologically acceptable salt of L-carnitine, acetyl L-carnitine and propionyl L-carnitine is selected from group comprising: chloride; bromide; iodide; aspartate, particularly acid aspartate; citrate, particularly acid citrate; tartrate; phosphate, particularly acid phosphate, fumarate particularly acid fumarate; glycerophosphate; glucose phosphate, lactate; maleate, particularly acid maleate; orotate; oxalate, particularly acid oxalate; sulphate, particularly acid sulphate; trichloroacetate, trifluoroacetate and methanesulphonate.

7. The composition of claim 1 further including food supplements, vitamins, co-enzymes and mineral substances.

8. A method of suppressing withdrawal symptoms and the craving for alcohol comprising administering to an individual an effective amount of a combination of L-carnitine, acetyl L-carnitine and propionyl L-carnitine or the pharmacologically acceptable salts thereof.

9. A method of preventing the abuse of alcohol in substantially healthy individuals, said method comprising administering to an individual an effective amount of a combination of L-carnitine, acetyl L-carnitine and propionyl L-carnitine or the pharmacologically acceptable salts thereof.

10. The method of claim 8 or 9 wherein the molar ratio L-carnitine:acetyl L-carnitine:propionyl L-carnitine or the pharmacologically acceptable salts thereof ranges from 6:4:1 to 3:2:1.

11. The method of claim 10, wherein the molar ratio is 5:4:1.

12. The method of claim 8 or 9 wherein a unit dosage is administered comprising from 0.44 to 0.66 g L-carnitine inner salt; 0.44 to 0.66 g of acetyl L-carnitine inner salt; and from 0.12 to 0.18 g of propionyl L-carnitine inner salt or equimolar amounts of the pharmacologically acceptable salts thereof.

13. The method of claim 8 or 9 wherein the pharmacologically acceptable salt of L-carnitine, acetyl L-carnitine and propionyl L-carnitine is selected from group consisting of chloride, bromide, iodide, aspartate, citrate, tartrate, phosphate, fumarate, glycerophosphate, glucose phosphate, lactate, maleate, orotate, oxalate, sulphate, trichloroacetate, trifluoroacetate and methanesulphonate.

* * * * *